US006537360B2

(12) United States Patent
Miyama et al.

(10) Patent No.: US 6,537,360 B2
(45) Date of Patent: Mar. 25, 2003

(54) TOOTH COATING COMPOSITION AND OVER-COATING COMPOSITION THEREFOR

(75) Inventors: Torao Miyama, Tokyo (JP); Takashi Matsumoto, Tokyo (JP); Kaoruko Urai, Tokyo (JP); Kichizo Tanaka, Tokyo (JP); Kenji Inagaki, Chiba (JP); Harumi Aida, Chiba (JP)

(73) Assignee: Hanix Co., Ltd., Tokyo (JP)

( * ) Notice: Subject to any disclaimer, the term of this patent is extended or adjusted under 35 U.S.C. 154(b) by 104 days.

(21) Appl. No.: 09/816,312

(22) Filed: Mar. 26, 2001

(65) Prior Publication Data

US 2001/0037750 A1 Nov. 8, 2001

(30) Foreign Application Priority Data

Mar. 31, 2000 (JP) ........................................ 2000-096339

(51) Int. Cl.$^7$ .................................................. A61K 6/08
(52) U.S. Cl. .......................... 106/35; 424/49; 523/115; 523/113
(58) Field of Search ............................ 106/35; 424/49; 523/115, 113

(56) References Cited

U.S. PATENT DOCUMENTS 4,141,144 A * 2/1979 Lustgarten ............... 433/217.1
5,693,313 A * 12/1997 Shiraishi et al. ............... 424/49
6,048,913 A * 4/2000 Yamagishi et al. ......... 523/118

FOREIGN PATENT DOCUMENTS

| JP | 41-11000 | 6/1966 |
| JP | 45-27225 | 9/1970 |

* cited by examiner

Primary Examiner—C. Melissa Koslow
(74) Attorney, Agent, or Firm—Browdy and Neimark, P.L.L.C.

(57) ABSTRACT

A tooth coating composition comprises a component A including a reactive metallic oxide; and a component B of water, which are mixed with each other when using the tooth coating composition, wherein at least one of the component A and the component B comprises a polycarboxylic acids, a reaction retarder and a coating film-softening agent. Specifically, the reactive metallic oxide may be zinc oxide or the like, the polycarboxylic acid may be polyacrylic acid or the like, the reaction retarder may be calcium hydrogen phosphate or the like, and the coating film-softening agent may be polymethyl methacrylate or the like. The coated film formed from the tooth coating composition has a color approximate to the color of natural teeth, and causes little irritation to mouths. In addition, the coating film has high durability and easy removability after use, so that it can be easily used by ordinary consumers.

18 Claims, No Drawings

TOOTH COATING COMPOSITION AND OVER-COATING COMPOSITION THEREFOR

FIELD OF THE INVENTION

The present invention relates to a tooth coating composition to be applied over teeth for attaining improvements in dental health and/or appearance.

BACKGROUND OF THE INVENTION

As people age, their teeth tend to turn to a natural yellow or dark color. Also, yellowing or darkening of teeth is sometimes caused by dental treatments. It is substantially impossible to remedy such undesirable cosmetic phenomena merely by brushing one's teeth with tooth powder or toothpaste. Currently, one general approach is to apply a coating film over the teeth to attempt to remedy these undesirable phenomena.

The tooth coating compositions for applying such tooth coating films that have been previously known include those comprising cyanoacrylate or derivatives thereof as main components, which were developed by the present inventors and disclosed in Japanese Patent Publication No. Sho 41-11000 and Japanese Patent Publication No. Sho 45-27225; and those comprising shellac resin as main components. Recently, there have been developed several examples of coating agents for teeth using dental cements such as glass ionomer cement, carboxylate cement and the like.

The tooth coating compositions comprising cyanoacrylate as their main component have, however, a defect in that after the coating has been applied and later becomes damaged so as to be unsightly, it is very difficult to remove from the teeth because the coating film formed using a tooth coating agent has extremely strong adhesion to the teeth and there is no suitable removing agent therefor.

On the other hand, the tooth coating agents using shellac resin as their main component are likely to peel off from teeth when the user is having a meal. Such a coating agent has further defects such as unnatural whitening to a plaster-like coloroccurring several hours after application, and unevenness of color generated in each application due to poor dispersing stability of pigments.

Those compositions based on dental cements also have a problem in removal because they also have strong adhesion to the teeth, and removal thereof requires special skills. Thus, the tooth coating agents using the dental cements cannot be easily used by ordinary consumers due to the extremely difficult removing operation.

SUMMARY OF THE INVENTION

Consequently, an object of the present invention is to provide a tooth coating composition kit that provides a color approximate to the color of natural teeth, causes little irritation to mouth, and attains both high durability and easy removability after use so that it can be easily utilized by ordinary consumers.

As a result of intensive research carried out by the present inventors in order to solve the above-mentioned problems and thus achieving the above-mentioned object, the present inventors have found that a tooth coating composition which provides a color approximate to the color of natural teeth, causes little irritation to mouth, and attains high durability and easy removability after use so that it can be easily handled by ordinary consumers, are obtained according to the present invention by using polycarboxylic acids, reactive metallic oxides, a coating film-softening agent and a reaction retarder.

The durability and natural tooth color of the tooth coating composition according to the present invention can, however, be further improved to even better inhibit any unnatural white or turbid appearance after several hours have elapsed from application of a coating film over teeth. In order to accomplish this improvement, the present inventors further developed an over-coating composition to be applied over the aforementioned film formed of the teeth coating composition applied to teeth. The combination use of the tooth coating composition and the over-coating composition therefor can realize a tooth coating film without occurrence of whitening or turbidity.

Specifically, the tooth coating composition kit according to the present invention comprises a component A comprising at least a reactive metallic oxide; and a component B comprising at least water; these components are mixed with each other when using the tooth coating composition. The tooth coating composition is characterized in that a polycarboxylic acid, a reaction retarder and a coating film-softening agent are contained in at least one of the component A and the component B.

The over-coating composition for the tooth coating composition according to the present invention is characterized in that it comprises as its main component one or more coating film-forming substances selected from the group consisting of shellac resin, polyvinyl acetate resin and alkyl acrylate copolymers.

DETAILED DESCRIPTION OF THE PREFERRED EMBODIMENTS

The details of the present invention will be described hereinafter with reference to but not limited to the following preferred embodiments.

Polycarboxylic acids have carboxyl groups within molecules and react with reactive metallic oxides under acidic conditions and in the presence of water, whereby tenacious coating films are formed. The durability of the coating film becomes lower when the average molecular weight of the polycarboxylic acid is less than 4000, whereas the applying properties would be deteriorated due to an over-great viscosity when the average molecular weight of the polycarboxylic acid exceeds 10000. As a consequence, the average molecular weight of the polycarboxylic acids is preferably within a range from 4000 to 9000, and preferably about 8000.

The polycarboxylic acids used in the tooth coating composition according to the present invention are one or more compounds selected from the group consisting of polymers and copolymers of acrylic acid, methacrylic acid, maleic acid and itaconic acid. Concrete examples thereof include polyacrylic acid, polymethacrylic acid, acrylic acid-methacrylic copolymers, acrylic acid-itaconic acid copolymers, acrylic acid-maleic acid copolymers, polymaleic acids, polyitaconic acids, etc.

The polycarboxylic acid reacts with the reactive metallic oxide in the presence of water to form a tenacious coating film. For practical use, the reactive metallic oxides in the tooth coating composition according to the present invention is one or more metallic oxides selected from the group consisting of zinc oxide, calcium oxide and aluminum oxide. Zinc oxide has rich reactivity and therefore can be used by itself. On the other hand, the reactivity of both calcium oxide and aluminum oxide is comparatively poor, and therefore using a mixture thereof especially with zinc oxide is recommendable.

In addition to the metallic acids stated above, magnesium oxide and silicon oxide have a similar effect. However, they need to be used in combination with at least one other metallic oxide, preferably zinc oxide, since the practical effects thereof are extremely small when they are singly used. In particular, magnesium oxide and/or silica oxide can be used to reduce the quantity of zinc oxide.

The content of the metallic oxides with respect to the entire composition (i.e., the total amount of the component A and the component B) is preferably within a range from 0.2% to 35%. If the content is less than 0.2%, the coating film is unduly week and easily peeled. On the other hand, if the content is greater than 35%, the coating film becomes hardened too quickly, thus causing difficulty in the applying operation. The content of the metallic oxides with respect to the entire composition is more preferably within a range of from 2% to 15%.

The content of the polycarboxylic acid with respect to the total amount of the component A and the component B is preferably within a range from 5% to 40%, especially from 10% to 20%. If the content is less than 5%, the coating film has the luster without the gloss and is unduly week and easily peeled. On the other hand, if the content is greater than 40%, the coating film does not dry well and it tends to dissolve in the mouth and becomes easily removed.

In the tooth coating composition according to the present invention, the reactive metallic oxides simultaneously have properties as coating film-forming-components and also properties as pigments. Favorite colors of individual consumers can be obtained by selecting suitable grain sizes of the reactive metallic oxides in the tooth coating composition. For example, the coating film shows a light white color when an average grain size of the reactive metallic oxides is 0.1/$\mu$m or smaller, and a dense white color is obtained when the average grain size of the reactive metallic oxides exceeds 0.5 $\mu$m.

The reaction retarder in the tooth coating composition according to the present invention has the function of adjusting the time of the reaction between the reactive metallic oxides and the polycarboxylic acids. Specifically, due to the action of the reaction retarder, a sufficient period of time for mixing operation can be provided by retarding the period of time until the hardening of the coating film occurs.

The reaction retarder used in the tooth coating composition according to the present invention is one or more compounds selected from a group consisting of alkali metal salts of phosphoric acid, alkaline earth metal salts of phosphoric acid, citric acid and alkali metal salts of citric acid. Specifically, preferable examples of the reaction retarder used in the present invention include calcium hydrogen phosphate, sodium monohydrogen phosphate, sodium dihydrogen phosphate, trisodium phosphate, citric acid, sodium citrate, etc. A content of the reaction retarder with respect to the entire composition (i.e. a total amount of the component A and the component B) is preferably within a range from 0.02% to 45%.

Calcium hydrogen phosphate, which is preferably used as the reaction retarder of the tooth coating composition according to the present invention, has conventionally been used in tooth powder, toothpaste and foods as a component to be suitably and safely used in the mouth. Further, various grain sizes of calcium hydrogen phosphate provide various effects on the color of the coating film. That is, when the average-grain size of calcium hydrogen phosphate exceeds 20 $\mu$m the coating films begins to show an unnatural white color, and the surface of the coating becomes rough and loses gloss, thus causing a discomfortable feeling in the mouth.

When the average grain size of calcium hydrogen phosphate is 20 $\mu$m or smaller, the coating film shows a color approximate to the color of natural teeth and the surface of the coating film is smooth and glossy. Therefore, 20 $\mu$m is considered to be an upper limit of the average grain size of calcium hydrogen phosphate. On the other hand, there is no particularly lower limit for the average grain size of calcium hydrogen phosphate. A content of calcium hydrogen phosphate with respect to the entire composition (i.e., a total amount of the component A and the component B) is preferably within a range from 2% to 45%, and further more preferably within a range from 4% to 30%.

When sodium monohydrogen phosphate, sodium dihydrogen phosphate, trisodium phosphate, citric acid, sodium citrate or the like is used as the reaction retarder rather than the calcium hydrogen phosphate, the content thereof with respect to the entire composition (i.e., a total amount of the component A and the component B) is preferably within a range from 0.02% to 8%, and further more preferably within a range from 0.04% to 2.5%. Use of these reaction retarders results in a coating which is not as hard as the coating film obtained using calcium hydrogen phosphate.

The softening agent used in the tooth coating composition according to the present invention is one or more compounds selected from the group consisting of particulate polymethyl methacrylate; cellulose ethers and salts thereof; and thickening polysaccharides. Preferable examples of the softening agent used in the present invention include polymethyl methacrylate; cellulose ethers such as methyl cellulose, propyl cellulose, carboxymethyl cellulose, carboxyethyl cellulose, hydroxyethyl cellulose, hydroxypropyl cellulose and salts thereof; and thickening polysacharides such as xanthan gum, guar gum, carageenan, sodium alginate, etc. A content of the softening agent with respect to the entire component (i.e. a total amount of the component A and the component B) is preferably within a range from 0.01% to 55%.

Particularly, polymethyl methacrylate, which is a polymer of methyl methacrylate, has substantially no adhesion to teeth when it is used by itself. However, in the tooth coating composition according to the present invention, polymethyl methacrylate in particulate form provides the coating film with softness and simultaneously acts as an agent for inhibiting the coating film from whitening caused by the deterioration with age of the coating film.

Polymethyl methacrylate begins to exhibit the effect as a softening agent for the tooth coating film when its content with respect to the entire composition (i.e., a total amount of the component A and the component B) reaches about 3%. When the content of polymethyl methacrylate is less than about 3%, the coating film would be too hard to be peeled from teeth. Further, polymethyl methacrylate begins to show the effect of inhibiting the coating film from whitening due to deterioration with age of the coating film when its content reaches 10% and greater. However, when the content exceeds 45%, the surface of the coating film loses gloss, thus becoming somewhat unsatisfactory in view of appearance. Further, when the content exceeds 55%, the composition substantially has no adhesion to the teeth, thus failing in functioning as a tooth coating composition. Consequently, the content of polymethyl methacrylate with respect to the entire composition (i.e., a total amount of the component A and the component B) is suitably within a range of 3% to 55%, and preferably within a range from 10% to 45%.

Further, when taking into consideration the balance of various properties of the coating film formed of the coating composition according to the present invention such as strength, adhesion to teeth, ease of peeling from teeth after use, prevention of unnatural whitening and aesthetic aspects, the content of polymethyl methacrylate is most preferably adopted to be within a range of 20% to 35%.

Similar to zinc oxide and calcium hydrogen phosphate, polymethyl methacrylate also provides a great effect on the color of the coating film, and again large grain sizes are not preferable. There is no particularly lower limit for the grain size of polymethyl methacrylate. When the grain size of polymethyl methacrylate exceeds 200 μm, the white color of coating film becomes dense, thus causing an unnatural color in the whole coating film, and simultaneously making the surface of the coating film rough and poor in gloss. Therefore, an upper limit of the grain size of polymethyl methacrylate used in the tooth coating composition according to the present invention is 200 μm.

When the cellulose ethers or thickening polysaccharides are used as the softening agent for the coating film rather than polymethyl methacrylate, the content thereof with respect to the entire composition (i.e., a total amount of the component A and the component B) is preferably within a range from 0.01% to 5%, and more preferably within a range from 0.05% to 3%. However, control of color is more difficult with these softening agents.

The over-coating composition according to the present invention is applied over the tooth coating composition according to the present invention after the tooth coating composition has been applied over teeth and at least partially dried, whereby gloss of the coating film surface is increased, and the whitening phenomenon due to deterioration with age of the tooth coating composition that forms a grounding layer of the coating film is suppressed.

The over-coating composition according to the present invention comprises, as its main component, one or more coating film-forming substances selected from the group consisting of shellac resin, polyvinyl acetate resin and alkyl acrylate copolymers. The above-mentioned coating film-forming substances are used in the state of being dissolved in water, alcohol or both. They may also be used in the forms of emulsion or dispersion. Shellac resin is preferably dissolved in alcohol since it has poor solubility in water.

The alkyl acrylate copolymers are copolymers composed of two of more compounds preferably selected from alkyl acrylates (C1 to C4, C8), alkyl methacrylates (C1 to C4, C8), acrylic acid and methacrylic acid. As indicated above, in general water or alcohol is contained therein as a carrier. Further, drying time can be shortened by adding alcohol as a quick drying agent.

It will be evident for those skilled in the art that various components that can be used in the mouth such as aromatics, bactericides, antiseptics, buffers, pH regulators, surface active agents, bad breath inhibitors, sweetening agents, antioxidants, thickeners, emulsifying agents, luster reflex agents and so on can be added to the tooth coating composition and/or its over-coating composition according to the present invention, if desired.

In addition, a luster reflex agent can be added to either or both of the tooth coating composition and the over-coating composition, whereby the films on the teeth can be adjusted to emit various glosses under reflection of light, thus providing the coated film with an aesthetic effect.

The luster reflex agent is one or more materials selected from a group consisted of epoxy resin coated polyethyleneterephthalate/aluminum laminated film powder, polyethyleneterephthalate/polymethylmethacrylate laminated film powder, polyethyleneterephthalate/polyolefin laminated film powder, polyethylene/polyester laminated film powder, polyethylene/polyethyleneterephthalate laminated film powder and polyethyleneterephthalate/gold laminated film powder.

The present invention will be described in more details with reference to the following examples.

EXAMPLE 1

|  | % by weight |
|---|---|
| Component A |  |
| Polyacrrylic acid | 24.3 |
| (average molecular weight: 8000) |  |
| Zinc oxide | 9.7 |
| (average grain size: 0.04 μm |  |
| Calcium hydrogen phosphate used in toothpaste | 14.6 |
| (Average grain size: 3 μm) |  |
| Polymethyl methacrylate | 48.5 |
| (average grain size: 1 μm) |  |
| Hydroxypropyl cellulose | 2.4 |
| Sodium dihydrogen phosphate | 0.5 |
| (component B) |  |
| Water | 100.0 |

0.10 g of water as the component B was added to 0.2 g of the above-stated component A, and was well blended to obtain a tooth coating composition. Then, a suitable amount of the tooth coating composition thus obtained was applied with a brush or pen to the teeth. The coating film formed of the tooth coating composition composed of the above-stated component A and component B showed a very light white color and remained without peeling from teeth for more than 24 hours during which the user had meals as usual. However, several defects still existed in this example. Specifically, the surface of the coating film gave a slightly rough feeling when it was touched by a tongue. In addition, the surface of the coating film lost gloss after a certain long period of time elapsing from the application of the coating composition, and then the whole coating film became dense white and turbid.

EXAMPLE 2

| over-coating composition | % by weight |
|---|---|
| Alkyl acrylate copolymer solution | 82.97 |
| (30% aqueous solution) |  |
| Ethyl alcohol | 16.00 |
| Aromatic | 1.99 |
| Char carbonizing agent (flavonoid) | 0.01 |
| (bad breath inhibitor) |  |
| Sodium saccharate (sweetening agent) | 0.01 |
| Sodium dehydroacetate (antiseptic) | 0.01 |

The tooth coating composition according to example 1 was applied onto the surfaces of the teeth and dried for about 5 minutes. Thereafter, the above-stated over-coating composition was applied with another pen or brush over the film formed of the applied tooth coating composition, and further dried for another 3 minutes.

The coating film was quickly dried and therefore the entire operation time was successfully shortened by adding 16.00% of ethyl alcohol into the over-coating composition.

A coating film thus obtained exhibited a very light white color and gloss approximate to natural teeth. Further, the surface of the coating film was smooth and substantially did not give an unconformable feeling in the mouth. In addition, unnatural whitening of the under coating composition was completely prevented by the over-coating composition. Furthermore, a substantially sound state of the coating film remained for 48 hours without its surface being flawed or peeling off due to meals or the like. Ever after a long period of time, gloss could be provided by re-applying the over-coating composition for many times so as to recover the desired surface state of the coating film. Furthermore, the coating film could easily be removed with the fingernails or an earpick when the user wanted to peel off the coating film from teeth.

EXAMPLE 3

|  | % by weight |
|---|---|
| Component A | |
| Polyacrylic acid | 25.00 |
| (average molecular weight: 8000) | |
| Zinc oxide | 8.0 |
| (average grain size: 0.04 μm) | |
| Calcium hydrogen phosphate used in toothpaste | 15.00 |
| (average grain size: 3 μm) | |
| Polymethyl methacrylate | 50.00 |
| (average grain size: 1 μm) | |
| Magnesium oxide | 2.0 |
| (component B) | |
| Water | 99.0 |
| Sodium dihydrogen phosphate | 0.7 |
| Carageenan | 0.2 |
| Conium benzal chloride (5% aqueous solution) | 0.1 |
| (over-coating composition) | |
| Shellac resin (50% ethyl alcohol solution) | 20.0 |
| Ethyl alcohol | 79.8 |
| Aromatic | 0.02 |

0.14 g of the component B was added 0.2 g of the above-described component A. The mixture of the components A and B was further mixed with a brush to obtain a tooth coating composition, and then a suitable amount of this tooth coating composition was applied over surfaces of teeth.

After the applied tooth coating composition was dried for about 5 minutes, the above over-coating composition was applied over the tooth coating composition with another brush or pen and then dried for another 3 minutes. The coating film thus obtained exhibited a light white color and good durability for 30 hours or longer even though the user took meals as usual. Further, the addition of conium benzal chloride, which has also been used in tooth brushing agents, to the component B adds a caries inhibiting agent to further protect the teeth. Further, the coating film according to this example could easily be removed with fingernails or an earpick when the user wanted to peel off the coating film from his teeth.

EXAMPLE 4

|  | % by weight |
|---|---|
| Component A | |
| Zinc oxide | |
| (average grain size: 0.1 μm) | 10.0 |
| Calcium hydrogen phosphate used in toothpaste | 34.0 |
| (average grain size: 3 μm) | |
| Polymethyl methacrylate | 56.0 |
| (average grain size: 1 μm) | |
| Component B | |
| Acrylic acid-methacrylic acid copolymer | 95.55 |
| solution | |
| (average molecular weight: 9000) | |
| (30% aqueous solution) | |
| Water | 3.00 |
| Na$_3$PO$_4$.12H$_2$O | 1.00 |
| Sodium carboxymethyl cellulose | 0.30 |
| Sodium Fluoride | 0.15 |
| Over-coating composition | |
| Alkyl acrylate solution | 91.45 |
| (30% aqueous solution) | |
| Water | 7.00 |
| Aromatic | 1.50 |
| Sodium saccharate | 0.05 |

0.16 g of the component B was added to 0.2 g of the above-stated component A. The mixture of the components A and B thus obtained was well mixed with a brush to obtain the tooth coating composition, and then a suitable amount of this tooth coating composition was applied over surfaces of teeth.

After the applied tooth coating composition was dried for about 5 minutes, the over-coating composition comprising the above-listed components was applied over the tooth coating composition with another brush or pen and then dried for another 3 minutes. The coating film thus obtained exhibited a white color denser than the color obtained in example 1, thus achieving excellent concealing ability. Therefore, the coating film according to this application is suitable for remarkably discolored teeth. Further, the addition of sodium fluoride into the component B provides a dental caries inhibiting effect.

Furthermore, this coating film did not peel off easily during meals or the like, and a substantially sound state thereof remained for 48 hours. On the other hand, this coating film could be easily removed from the user's teeth with the user's finger nails or an earpick when the user wanted to peel it off.

EXAMPLE 5

|  | % by weight |
|---|---|
| Component A | |
| Zinc oxide | 6.0 |
| (average grain size: 0.7 μm) | |
| Silicon oxide | 16.5 |
| Calcium hydrogen phosphate used in toothpaste | 44.3 |
| (average grain size: 3 μm) | |
| Polymethyl methacrylate | 33.1 |

|                                                                                  | % by weight |
| --- | --- |
| (average grain size: 1 μm)                                                       |             |
| Methyl cellulose                                                                 | 0.1         |
| Component B                                                                      |             |
| Acrylic acid-methacrylic acid copolymer solution (average molecular weight: 8000) (30% aqueous solution) | 95.1 |
| Water                                                                            | 2.0         |
| Ethyl alcohol                                                                    | 2.0         |
| Sodium monohydrogen phosphate                                                    | 0.8         |
| Char carbonization liquid                                                        | 0.1         |
| Over-coating composition                                                         |             |
| Polyvinyl acetate resin                                                          | 20.00       |
| Ethyl alcohol                                                                    | 71.00       |
| Water                                                                            | 7.95        |
| Aromatic                                                                         | 1.00        |
| Sodium saccharate                                                                | 0.05        |

0.12 g of the component B was added to 0.2 g of the above-stated component A. The mixture of the components A and B thus obtained was well mixed with a brush to obtain a tooth coating composition, and then a suitable amount of this tooth coating composition was applied over surfaces of teeth.

After the applied tooth coating composition was dried for about 5 minutes, the over-coating composition comprising the above-listed components was applied over the tooth coating composition with another brush or pen and then dried for another 3 minutes. The coating film thus obtained exhibited a white color even denser than the color obtained in example 4. Therefore, the coating film according to this example is suitable for concealing blackened teeth.

Furthermore, this coating film did not peel off easily during meals or the like, and a substantially sound state thereof remained for 48 hours. On the other hand, this coating film also could be easily removed with nails or an earpick when the user wanted to peel it off from his teeth.

EXAMPLE 6

|                                                                                  | % by weight |
| --- | --- |
| Component A                                                                      |             |
| Zinc oxide (average grain size: 0.04 μm)                                         | 11.0        |
| Silicon oxide                                                                    | 28.0        |
| Magnesium oxide                                                                  | 9.0         |
| Acrylic acid-itaconic acid copolymer (average molecular weight: 8000)            | 51.3        |
| Sodium citrate                                                                   | 0.7         |
| Component B                                                                      |             |
| Water                                                                            | 96.15       |
| Sodium alginate                                                                  | 0.50        |
| Ethyl alcohol                                                                    | 3.00        |
| Methylparaben (antiseptic)                                                       | 0.10        |
| Propylparaben (antiseptic)                                                       | 0.05        |
| Aromatic                                                                         | 0.20        |
| Over-coating composition                                                         |             |
| Alkyl acrylate copolymer solution (30% aqueous solution)                         | 60.78       |
| Ethyl alcohol                                                                    | 4.00        |
| Char carbonization liquid                                                        | 0.20        |
| Epoxy resin coated polyethyleneterephthalate/aluminum laminated film powder      | 35.00       |
| Sodium saccharate                                                                | 0.02        |

0.10 g of the component B was added to 0.2 g of the above-stated component A. The mixture of the components A' and B thus obtained was well mixed with a brush to obtain a tooth coating composition, and then a suitable amount of this tooth coating composition was applied over surfaces of teeth.

After the applied tooth coating composition was dried for about 5 minutes, the over-coating composition comprising the above-listed components was applied over the tooth coating composition with another brush or pen and then dried for another 3 minutes. Owing to the epoxy resin coated polyethyleneterephthalate/aluminum laminated film powder (having a crystal color) mixed in the over-coating composition, the coating film showed a beautiful color, thus it could be used for ornamental purposes in addition to the purpose of concealing the discoloration of teeth.

Furthermore, this coating film did not peel off easily during meals or the like, and a substantially sound state thereof remained for 48 hours. On the other hand, this coating film could be easily removed with the user's fingernails or an earpick when the user wanted to peel it off from his teeth.

EXAMPLE 7

|                                                                                  | % by weight |
| --- | --- |
| Component A                                                                      |             |
| Calcium oxide                                                                    | 21.4        |
| Aluminum oxide                                                                   | 10.2        |
| Acrylic acid-maleic acid copolymer (average molecular weight: 8000)              | 44.0        |
| Polymethyl methacrylate                                                          | 24.3        |
| Carboxyethyl cellulose                                                           | 0.1         |
| Component B                                                                      |             |
| Water                                                                            | 77.1        |
| Calcium hydrogen phosphate used in toothpaste (average grain size: 3 μm)         | 21.0        |
| Citric acid                                                                      | 1.4         |
| Aromatic                                                                         | 0.5         |
| Over-coating composition                                                         |             |
| Alkyl acrylate copolymer liquid (30% aqueous solution)                           | 55.8        |
| Water                                                                            | 14.0        |
| Polyethyleneterephthalate/polymethylmethacrylate laminated film powder           | 29.0        |
| Aromatic                                                                         | 1.2         |

0.14 g of the component B is added to 0.2 g of the above-stated component A. The mixture of the components A and B thus obtained is well mixed with a brush to obtain a tooth coating composition, and then a suitable amount of this tooth coating composition is applied to surfaces of teeth.

After the applied tooth coating composition is dried for about 7 minutes, the over-coating composition comprising the above-listed components is applied over the tooth coating composition with another brush or pen and then dried for another 3 minutes. Comparing to the coating film formed of the tooth coating composition having zinc oxide in the component A, the coating film obtained in this example is somewhat inferior in strength and durability. On the other hand, the film coating obtained in this example had an advantage that it could be more easily removed with nails or an earpick when the user wanted to peel it off from teeth.

Due to the addition of the polyethyleneterephthalate/polymethylmethacrylate laminated film powder, the coating film emitted an iridescent gloss under reflection of light, and thus providing the coating film with an aesthetic effect.

EXAMPLE 8

| | % by weight |
|---|---|
| Component A | |
| Zinc oxide (average grain size: 0.04 μm) | 10.6 |
| Polyacrylic acid (average molecular weight: 4000) | 10.0 |
| Polymaleic acid (average molecular weight: 8000) | 21.4 |
| Calcium hydrogen phosphate used in toothpaste (average grain size: 3 μm) | 20.5 |
| Polymethyl methacrylate | 37.5 |
| Component B | |
| Water | 85.9 |
| Sodium dihydrogen phosphate | 1.1 |
| Xanthan gum | 0.2 |
| Guar gum | 0.1 |
| Polyethyleneterephthalate/polymethylmethacrylate laminated film powder | 12.0 |
| Aromatic | 0.7 |
| Over-coating composition | |
| Alkyl acrylate copolymer solution (30% aqueous solution) | 100.0 |

0.12 g of the component B was added to 0.2 g of the above-stated component A. The mixture of the components A and B thus obtained was well mixed with a brush to obtain a tooth coating composition, and then a suitable amount of this tooth coating composition was applied over surfaces of teeth.

After the applied tooth coating composition was dried for about 5 minutes, the over-coating composition comprising the above-listed components was applied over the tooth coating composition with another brush or pen and then dried for another 3 minutes. The coating film obtained in the present example showed substantially the same light white color as that of the coating film obtained in example 1.

Further, due to the addition of polyacrylic acid having an average molecular weight of 4000, the strength of the coating film was somewhat reduced, whereas a rich flexibility was attained and the coating film could be easily peeled off from teeth.

The tooth coating composition and over-coating composition therefor according to the present invention can achieve the following advantages:

(1) The polycarboxylic acids and the reactive metallic oxides react with each other when the component A and the component B of the tooth coating composition according to the present invention are mixed with each other for use, and therefore a firm coating film is formed over surfaces of teeth.

(2) Operation of applying the tooth coating composition over surfaces of teeth can be made easier by adding the reaction retarder into the tooth coating composition so as to slow the rate of the reaction between the polycarboxylic acids and the reactive metallic oxides.

(3) Owing to the addition of the coating film-softening agent into the tooth coating composition, the hardness of the coating film can be adjusted so as to prevent the coating film from becoming damaged when the user takes foods. Further, the coating film can be formed such that it is easily removable from teeth after use.

(4) When the over-coating composition, which comprises the coating film-forming substances such as shellac resin, polyvinyl acetate resin, alkyl acrylic acid copolymers or the like, is further applied over the coating film formed of the tooth coating composition, according to the present invention as is preferred, so that a smooth surface of the coating film without any rough feel is obtained, the color as well as the gloss of the coating film is improved, the durability of the coating film is increased, and the whitening phenomenon of the under coating film is suppressed.

(5) The over-coating composition, which comprises coating film-forming substances such as shellac resin, polyvinyl acetate resin, alkyl acrylic acid copolymers or the like, is preferably further applied over the coating film formed of the tooth coating composition according to the present invention. The over-coating composition according to the present invention exhibits the function as a protection film until the under coating film is completely hardened, thus preventing the under coating film from peeling off.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

Thus the expressions "means to . . ." and "means for . . .", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

What is claimed is:

1. A tooth coating composition kit comprising a component A comprising at least one reactive metallic oxide; and a component B comprising at least water; said component A and said component B being mixed with each other when said tooth coating composition is to be used, said tooth coating composition being characterized in that at least one of said component A and said component B comprises a polycarboxylic acid, a reaction retarder and a coating film-softening agent.

2. A tooth coating composition kit according to claim 1 wherein said polycarboxylic acid is at least one compound selected from the group consisting of polymers and copolymers of acrylic acid, methacrylic acid, maleic acid and itaconic acid.

3. A tooth coating composition kit according to claim 1, wherein said reactive metallic oxide is at least one compound selected from the group consisting of zinc oxide, calcium oxide and aluminum oxide; said reaction retarder is at least one compound selected from the group consisting of alkali metal salts of phosphoric acid, alkaline earth metal salts of phosphoric acid, citric acid, and alkali metal salts of citric acid; and said coating film-softening agent is at least one compound selected from the group consisting of polymethyl methacrylate, cellulose esters and salts thereof, and thickening polysaccharides.

4. A tooth coating composition kit according to claim 1, wherein said component A comprises polyacrylic acid, zinc oxide, calcium hydrogen phosphate, polymethyl methacrylate, sodium dihydrogen phosphate and hydroxypropyl cellulose; and said component B comprises water.

5. A tooth coating composition kit according to claim 1, wherein an average molecular weight of said polycarboxylic acid is 4000 to 9000.

6. A tooth coating composition kit according to claim 1, wherein a content of the polycarboxylic acid with respect to the total amount of the component A and the component B is within a range from 5% to 40%.

7. A tooth coating composition kit according to claim 1, wherein a content of the reactive metallic oxide with respect to the total amount of the component A and the component B is within a range from 0.2% to 35%.

8. A tooth coating composition kit according to claim 1, wherein a content of the reaction retarder with respect to the total amount of the component A and the component B is within a range from 0.02% to 45%.

9. A tooth coating composition kit according to claim 1, wherein a content of the coating film softening agent with respect to the total amount of the component A and the component B is within a range from 0.01% to 55%.

10. A tooth coating composition according to claim 1, wherein at least one of the component A and the component B also comprises a luster reflex agent.

11. A tooth coating composition kit according to claim 10, wherein said luster reflex agent is selected from a group consisting of epoxy resin coated polyethyleneterephthalate/aluminum laminated film powder, polyethyleneterephthalate/polymethylmethacrylate laminated film powder, polyethyleneterephthalate/polyolefin laminated film powder, polyethylene/polyester laminated film powder, polyethylene/polyethyleneterephthalate laminated film powder, polyethyleneterephthalate/gold laminated film powder, and mixture thereof.

12. A tooth coating composition comprising a mixture of components A and B of claim 1.

13. The tooth coating composition kit of claim 1 further comprising an over-coating composition, said over-coating composition comprising as its main component one or more coating film-forming substances selected from the group consisting of shellac resin, polyvinyl acetate resin and alkyl acrylate copolymers.

14. The composition kit of claim 13, wherein said over-coating composition further comprises alcohol as a drying agent accelerator.

15. The composition kit of claim 13, wherein said over-coating composition further comprises a luster reflex agent.

16. The composition kit of claim 15, wherein in said over-coating composition, said luster reflex agent is one or more materials selected from the group consisting of epoxy resin coated polyethyleneterephthalate/aluminum laminated film powder, polyethyleneterephthalate/polymethylmethacrylate laminated film powder, polyethyleneterephthalate/polyolefin laminated film powder, polyethylene/polyester laminated film powder, polyethylene/polyethyleneterephthalate laminated film powder and polyethyleneterephthalate/gold laminated film powder.

17. A method of coating a tooth comprising mixing components A and B of claim 1, and applying the resultant mixture to the tooth.

18. A method of coating a tooth comprising mixing components A and B of claim 13, applying the resultant mixture to the tooth as a layer and at least partially drying said layer, and the applying said over-coating composition over said at least partially dried layer.

* * * * *